(12) United States Patent
Skranc et al.

(10) Patent No.: US 6,909,011 B2
(45) Date of Patent: Jun. 21, 2005

(54) PROCESS FOR PREPARING PROTECTED, ENANTIOMER-ENRICHED CYANOHYDRINS BY IN-SITU DERIVATIZATION

(75) Inventors: Wolfgang Skranc, Vienna (AT); Peter Poechlauer, Linz (AT); Irma Wirth, Enns (AT); Rudolf Neuhofer, Mittertreffling (AT); Herbert Mayrhofer, Engerwitzdorf (AT)

(73) Assignee: DSM Fine Chemicals Austria NFG GmbH & CO KG, Linz (AT)

( * ) Notice: Subject to any disclaimer, the term of this patent is extended or adjusted under 35 U.S.C. 154(b) by 0 days.

(21) Appl. No.: 10/325,923

(22) Filed: Dec. 23, 2002

(65) Prior Publication Data

US 2003/0129714 A1 Jul. 10, 2003

(30) Foreign Application Priority Data

Dec. 28, 2001  (AT) .......................................... 2044/2001

(51) Int. Cl.$^7$ ........................ C07C 253/16; C12P 13/16
(52) U.S. Cl. ........................ 558/351; 435/128
(58) Field of Search .................... 558/351; 435/128; 546/176, 330; 548/215, 240; 549/75; 544/242

(56) References Cited

U.S. PATENT DOCUMENTS

| | | | | |
|---|---|---|---|---|
| 4,414,218 A | * | 11/1983 | Au .............................. | 514/344 |
| 5,350,871 A | * | 9/1994 | Geluk et al. ................. | 558/351 |
| 6,225,095 B1 | * | 5/2001 | Pochlauer et al. .......... | 435/128 |
| 6,287,829 B1 | * | 9/2001 | Stutz de Raadt et al. ... | 435/155 |
| 6,337,196 B1 | * | 1/2002 | Kirchner et al. ............ | 435/128 |
| 2003/0129713 A1 | * | 7/2003 | Skranc et al. ............... | 435/117 |
| 2003/0129714 A1 | * | 7/2003 | Skranc et al. ............... | 435/128 |

OTHER PUBLICATIONS

Poirier et al., Unexpected formation of O–methoxycarbonyl cyanohydrin showing potential as a protective group of ketones. Synlett 1999, No. 9, pp. 1423–1425.*

* cited by examiner

Primary Examiner—Johann Richter
Assistant Examiner—Ebenezer Sackey

(74) Attorney, Agent, or Firm—Wenderoth, Lind & Ponack, L.L.P.

(57) ABSTRACT

A process for preparing protected, enantiomer-enriched cyanohydrins of the formula

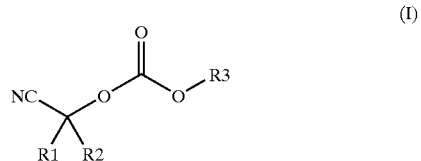

(I)

where R1 and R2 independently of one another can be an unsubstituted, monosubstituted or polysubstituted $C_1$–$C_{20}$-alkyl, $C_5$–$C_{20}$-aryl, $C_5$–$C_{20}$-heteroaryl, $C_5$–$C_{20}$-alkaryl, $C_5$–$C_{20}$-alkylheteroaryl or $C_5$–$C_{20}$-aralkyl radical or an unsubstituted, monosubstituted or polysubstituted $C_5$–$C_{20}$-heterocycle, or $C_5$–$C_{20}$-alkylheterocycle or together can be an unsubstituted or substituted $C_4$–$C_{20}$-alkylene radical, which can contain one or more heteroatoms in the chain, or one of the radicals is hydrogen, and R3 can be an unsubstituted or substituted $C_1$–$C_{20}$-alkyl, $C_5$–$C_{20}$-aryl or $C_5$–$C_{20}$-heteroaryl radical, by reacting an aldehyde or ketone of the formula

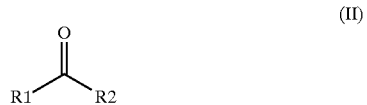

(II)

where R1 and R2 are defined as above, in the presence of an (R)- or (S)-hydroxynitrile lyase in an organic, aqueous or 2-phase system or in emulsion at a temperature of −5 to +40° C. with a carbonic ester nitrile of the formula

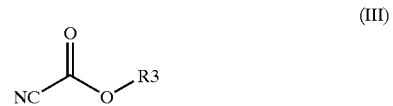

(III)

where R3 is defined as above.

10 Claims, No Drawings

PROCESS FOR PREPARING PROTECTED, ENANTIOMER-ENRICHED CYANOHYDRINS BY IN-SITU DERIVATIZATION

Process for preparing protected, enantiomer-enriched cyanohydrins by in-situ derivatization.

Cyanohydrins are of importance, for instance for the synthesis of alpha-hydroxy acids, alpha-hydroxy ketones, beta-amino alcohols, which are used to produce biologically active substances, for example, active pharmaceutical substances, vitamins or else pyrethroid compounds.

A cyanohydrin can be prepared by addition of prussic acid (HCN) to the carbonyl group of an aldehyde or a ketone, enantiomeric mixtures of unsymmetrical cyanohydrins being formed.

Many processes are based on carrying out the addition of HCN to the carbonyl group in the presence of a chiral catalyst, for example, a hydroxynitrile lyase. However, since HCN is an extremely toxic substance, attempts are constantly being made to avoid its direct use or direct handling. Compounds which have been used previously as alternatives to HCN as cyanide group donor are, for example, cyanohydrins of the general formula RR'C(OH)(CN), where R and R' independently of one another are hydrogen or an unsubstituted hydrocarbon group, or together are an alkylene group having 4 or 5 carbon atoms, where R and R' are not simultaneously hydrogen, for instance acetocyanohydrin. A further cyanide group donor is, for example, trimethylsilyl cyanide, which according to J. Am. Chem. Soc. 2001, 123, 9908–9909 is reacted with sugar derivatives at −40° C. in an absolute alcohol.

A further problem in the preparation of cyanohydrins is that cyanohydrins are inherently unstable and have a tendency to decompose in a reversal of their formation reaction, so that attempts have already been made to stabilize them by the most varied additions, in particular of acids, for instance sulfuric acid, phosphoric acid, HCl, toluenesulfonic acid, acetic acid, propionic acid etc.

In the case of some cyanohydrins, for instance in the case of acetophenone derivatives, furthermore, the equilibrium position of the reaction is somewhat unfavorable, as a result of which these cyanohydrins are only obtained in poor yields.

It was an object of the present invention to find a hydroxynitrile lyase-catalyzed process for preparing stable, enantiomer-enriched cyanohydrins, in which the direct use of prussic acid is avoided and which enables a shift of equilibrium to achieve high conversion rates.

Unexpectedly, this object was achieved by a process in which carbonic ester nitrites are used as cyanide group donors, as a result of which in-situ derivatization and thus stabilization of the enantiomer-enriched cyanohydrins proceeds.

The present invention therefore relates to a process for preparing protected, enantiomer-enriched cyanohydrins of the formula

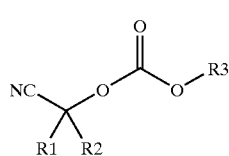

(I)

where R1 and R2 independently of one another can be an unsubstituted, monosubstituted or polysubstituted $C_1$–$C_{20}$-alkyl, $C_5$–$C_{20}$-aryl, $C_5$–$C_{20}$-heteroaryl, $C_5$–$C_{20}$-alkaryl, $C_5$–$C_{20}$-alkylheteroaryl or $C_5$–$C_{20}$-aralkyl radical or an unsubstituted, monosubstituted or polysubstituted $C_5$–$C_{20}$-heterocycle, or $C_5$–$C_{20}$-alkylheterocycle, or together can be an unsubstituted or substituted $C_4$–$C_{20}$-alkylene radical, which can contain one or more heteroatoms in the chain, or one of the radicals is hydrogen, and R3 can be an unsubstituted or substituted $C_1$–$C_{20}$-alkyl, $C_5$–$C_{20}$-aryl or $C_5$–$C_{20}$-heteroaryl radical, which process comprises reacting an aldehyde or ketone of the formula

(II)

where R1 and R2 are defined as above, in the presence of an (R)- or (S)-hydroxynitrile lyase in an organic, aqueous or 2-phase system or in emulsion at a temperature of −5 to +40° C. with a carbonic ester nitrile of the formula

(III)

where R3 is defined as above,
to give the corresponding O-protected, enantiomer-enriched cyanohydrins of the formula (I).

In the inventive process, aldehydes or ketones of the formula (II) are used as starting materials.

In the formula (II), R1 and R2 independently of one another can be an unsubstituted, monosubstituted or polysubstituted $C_1$–$C_{20}$-alkyl, $C_5$–$C_{20}$-aryl, $C_5$–$C_{20}$-heteroaryl, $C_5$–$C_{20}$-alkaryl, $C_5$–$C_{20}$-alkylheteroaryl or $C_5$–$C_{20}$-aralkyl radical or an unsubstituted, monosubstituted or polysubstituted $C_5$–$C_{20}$-heterocycle, or $C_5$–$C_{20}$-alkylheterocycle.

$C_1$–$C_{20}$-alkyl is taken to mean here saturated or monounsaturated or polyunsaturated unbranched, branched or cyclic, primary, secondary or tertiary hydrocarbon radicals. These are, for example, $C_1$–$C_{20}$-alkyl radicals, for instance methyl, ethyl, propyl, isopropyl, butyl, isobutyl, t-butyl, butenyl, butynyl, pentyl, cyclopentyl, isopentyl, neopentyl, pentenyl, pentynyl, hexyl, isohexyl, cyclohexyl, cyclohexylmethyl, 3-methylpentyl, 2,2-dimethylbutyl, 2,3-dimethylbutyl, octyl, cyclooctyl, decyl, cyclodecyl, dodecyl, cyclododecyl, etc.

Preference is given here to $C_1$–$C_{12}$-alkyl radicals, and particular preference to $C_1$–$C_8$-alkyl radicals.

The alkyl group can be unsubstituted, monosubstituted or polysubstituted by groups inert under the reaction conditions. Suitable substituents are, for example, unsubstituted or substituted aryl or heteroaryl groups such as phenyl, phenoxy or indolyl groups, halogen, hydroxyl, hydroxy-$C_1$–$C_5$-alkyl, $C_1$–$C_6$-alkoxy, aryloxy, preferably $C_6$–$C_{20}$-aryloxy, $C_1$–$C_6$-alkylthio, amino, alkylamino, preferably $C_1$–$C_6$-alkylamino, arylamino, preferably $C_6$–$C_{20}$-arylamino, ether, thioether, carboxylic ester, carboxamide, sulfoxide, sulfone, sulfonic acid, sulfonic ester, sulfinic acid, mercaptan, nitro or azido groups.

Aryl is preferably taken to mean $C_6$–$C_{20}$-aryl groups, for instance phenyl, biphenyl, naphthyl, indenyl, fluorenyl, etc.

The aryl group can be unsubstituted, monosubstituted or polysubstituted. Suitable substituents are again unsubstituted or substituted aryl or heteroaryl groups, such as phenyl, phenoxy or indolyl groups, halogen, hydroxyl, hydroxy-$C_1$–$C_5$-alkyl, $C_1$–$C_6$-alkoxy, aryloxy, preferably $C_6$–$C_{20}$-aryloxy, $C_1$–$C_6$-alkylthio, amino, alkylamino, preferably $C_1$–$C_6$-alkylamino, arylamino, preferably $C_6$–$C_{20}$-arylamino, ether, thioether, carboxylic ester, carboxamide, sulfoxide, sulfone, sulfonic acid, sulfonic ester, sulfinic acid, mercaptan, nitro or azido groups.

Alkaryl or alkylaryl are taken to mean alkyl groups which have an aryl substituent.

Aralkyl or arylalkyl relates to an aryl group having an alkyl substituent.

Heteroaryl or heterocycle are taken to mean cyclic radicals which contain at least one S, O or N atom in the ring. These are, for example, furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzoimidazolyl, purinyl, carbazolyl, oxazolyl, thiazolyl, isothiazolyl, 1,2,4-thiadiazolyl, isoxazolyl, pyrrolyl, quinazolinyl, pyridazinyl, phthalazinyl, morpholinyl, etc.

Functional O or N groups can if necessary be protected in this case.

The heteroaryl group or the heterocycle can be unsubstituted, monosubstituted or polysubstituted by the substituents already set forth above.

Alkylheteroaryl or alkylheterocycle are taken to mean here alkyl groups which are substituted by a heteroaryl group or by a heterocycle.

Preferably, R1 and R2 are a saturated, unbranched or branched $C_1$–$C_8$-alkyl radical, a benzyl radical or a phenyl radical, in which case the radicals can be unsubstituted, monosubstituted or polysubstituted by F, Cl, OH, carboxylic acid derivatives, such as carboxylic esters or carboxamides, amino, $C_1$–$C_6$-alkylamino, $C_6$–$C_{20}$-arylamino, $C_1$–$C_6$-alkoxy, $C_6$–$C_{20}$-aryloxy, or nitro.

R1 and R2, however, can also together be an unsubstituted or substituted $C_4$–$C_{20}$-alkylene radical, which can contain, in the chain, one or more heteroatoms selected from the group consisting of O, N or S, or an NR4R5 group, where R4 and R5 independently of one another can be H or $C_1$–$C_6$-alkyl. In this case the starting materials are cyclic ketones.

Preference is given to $C_4$–$C_7$-alkylene radicals which, depending on the ring size of the cyclic ketone, have at most 2 heteroatoms in the alkyl chain. The alkylene radical can, in addition, again depending on the ring size of the cyclic ketone, further have one or 2 double bonds, where in the case of a 5-membered ring this must not be conjugated with the carbonyl group.

The alkylene radical can in addition be monosubstituted or polysubstituted by the radicals set forth above.

In the starting materials used, however, one of the radicals R1 and R2 can also be hydrogen. In this case the starting materials are aldehydes.

According to the invention the desired starting material is reacted with a carbonic ester nitrile of the formula (III).

In the formula (III) R3 is an unsubstituted or substituted $C_1$–$C_{20}$-alkyl, $C_5$–$C_{20}$-aryl or $C_5$–$C_{20}$-heteroaryl radical. The alkyl radical here can be saturated, monounsaturated or polyunsaturated, unbranched, branched or cyclic. The aryl radicals and heteroaryl radicals are as defined above. Preferably, R3 is a $C_1$–$C_{12}$-alkyl radical. Suitable substituents are, for example, phenyl, $C_1$–$C_6$-alkyl, OH, halogen or a sulfoxy group.

Examples of suitable nitrites of the formula (III) are cyanoformic acid methyl ester, ethyl ester, 2,2,2-trichloroethyl ester, tert-butyl ester, benzyl ester, allyl ester, isobutyl ester, 2-ethylhexyl ester, p-menthyl ester, etc.

Carbonic ester nitrites of the formula (III) are commercially available or can be prepared, for example, from the corresponding halides and HCN or from an alkali metal cyanide, as described, for instance, in EP 0 136 145, Tetrahedron Letters No. 27, p. 2517 or J. Chem. Soc. Perkin Trans. 1, (15), 1729–35, 1993.

Per mole of aldehyde or keto group used, at least 1 mol, preferably 1 to 5 mol, particularly preferably 2 to 4 mol, of carbononitrile are added.

The inventive reaction takes place in an organic, aqueous or 2-phase system or in emulsion in the presence of a hydroxynitrile lyase as catalyst.

In the case of the enantioselective reaction in an aqueous system, an aqueous solution containing the corresponding HNL or buffer solution is used. Examples of these are acetate buffer, borate buffer, phthalate buffer, citrate buffer, phosphate buffer etc. or mixtures of these buffer solutions.

The pH of this solution is pH 2 to 8, preferably pH 2.5 to 6.5.

The organic diluent used can be water-immiscible or only slightly water-miscible aliphatic or aromatic hydrocarbons which may be halogenated, alcohols, ethers or esters or mixtures thereof. Preference is given to using methyl tert-butyl ether (MTBE), diisopropyl ether, dibutyl ether and ethyl acetate, or mixtures thereof.

The reaction, however, can also take place in a two-phase system or in emulsion.

Suitable HNLs are not only native but also recombinant (R)- and (S)-HNLs which are present either as such or immobilized.

Suitable (S)-hydroxynitrile lyases (HNLs) are native (S)-hydroxynitrile lyases, for example from manioc and *Hevea brasiliensis*, and recombinant (S)-HNLs. Preferably, the native HNL used is HNL from *Hevea brasiliensis*. Suitable recombinant (S)-HNLs are obtained, for example, from genetically modified microorganisms, for instance *Pichia pastoris, E. coli* or *Saccharomyces cerevisiae*.

Preference is given to using recombinant (S)-HNL from *Pichia pastoris*.

Suitable (R)-HNLs are, for example, (R)-hydroxynitrile lyases from *Prunus amygdalus, Prunus laurocerasus* or *Prunus serotina* or recombinant (R)-HNL. Preference is given to using (R)-hydroxynitrile lyase from *Prunus amygdalus* or a recombinant (R)-HNL.

Suitable (R)- and (S)-HNLs are disclosed, for example, by WO 97/03204, EP 0 969 095, EP 0 951 561, EP 0 927 766, EP 0 632 130, EP 0 547 655, EP 0 326 063, WO 01/44487 etc.

Per g of aldehyde or ketone, about 10 to 20 000 IU of activity of hydroxynitrile lyase are added, preferably about 100 to 10 000 IU of activity.

The reaction temperatures are about −5 to +40° C., preferably about 0 to 30° C.

Preferably, the inventive reaction is carried out in an aqueous system, the corresponding HNL being introduced first as aqueous solution, and depending on the HNL selected being adjusted to the desired pH using a suitable acid, for example using citric acid or a buffer, for instance acetate buffer, borate buffer, phthalate buffer, citrate buffer, phosphate buffer etc. or mixtures of these buffer solutions. The corresponding starting material of the formula (II) is then added and the reaction is started by adding the carbonic ester nitrile of the formula (III). In the course of this HCN develops which reacts under HNL-catalyzed addition with the starting material used initially to form a corresponding enantiomer-enriched cyanohydrin. Residual carbononitrile reacts with the enantiomer-enriched cyanohydrin to form the stable O-protected enantiomer-enriched cyanohydrin of the formula (I), with HCN again becoming free, which is used again for cyanohydrin formation.

However, the starting material can alternatively be introduced first and the corresponding HNL can then be added as aqueous solution.

The course of the reaction can be seen from the following diagram:

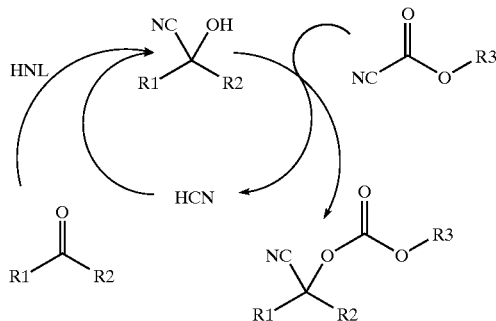

The inventive process makes possible here, owing to the chemical O-derivatization, a shift of equilibrium to the side of the desired end product, as a result of which, in particular in the case of cyanohydrins having an originally unfavorable equilibrium position, for instance acetophenone derivatives, a significantly higher conversion can be achieved compared with the prior art. At the same time, owing to the derivatization, stabilization of the cyanohydrins formed is achieved. A further advantage of the inventive process is the in-situ generation of HCN and the continuous resupply of HCN, with at the same time direct use of HCN being avoided. The derivatization reagent in this case, unexpectedly, does not decrease the activity of the HNL used, or decreases it only insignificantly.

EXAMPLE 1

HNL-catalyzed Reaction of Ethyl Cyanoformate with Benzaldehyde

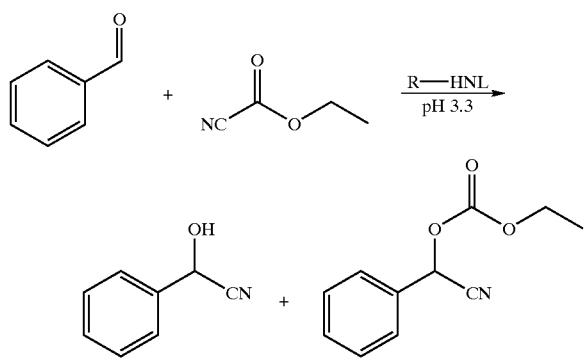

2.5 ml of recombinant R-HNL solution (300 IU/ml) were adjusted to pH 3.3 using a citric acid solution and were diluted with 2.5 ml of 50 mmol potassium phosphate/citrate buffer pH 3.3. 106 mg (1 mmol) of benzaldehyde were then added and the reaction was started by adding 297 µl (3 mmol) of ethyl cyanoformate. The reaction mixture was stirred at 25° C. and the formation of benzaldehyde cyanohydrin and O-ethoxycarbonyl cyanohydrin was followed by means of gas chromatography on a chiral phase (cyclodextrin column) and the corresponding enantiomeric purities were calculated.

Reaction Course:

| Reaction time | Benzaldehyde | Benzaldehyde cyanohydrin | | O-ethoxycarbonyl cyanohydrin | |
|---|---|---|---|---|---|
| (hours) | (area %) | (area %) | (% ee) | (area %) | (% ee) |
| 1 | 61 | 38 | 99.9 | 1 | 99.9 |
| 3 | 15 | 77 | 99.5 | 8 | 99.9 |
| 23 | 2 | 65 | 93.7 | 33 | 99.9 |
| 44.5* | <1 | 34 | 89.4 | 66 | 94.7 |

*After 26 hours, a further 297 µl (3 mmol) of ethyl cyanoformate were added.

Identification of the O-ethoxycarbonyl cyanohydrin:

$^1$H-NMR in $CDCl_3$, 300 MHz; δ 1.30–1.32(t, 3H), 4.21–4.36(m, 2H), 6.27 (s, 1H) 7.39–7.57(m, 5H)

What is claimed is:

1. A process for preparing protected, enantiomer-enriched cyanohydrins of the formula

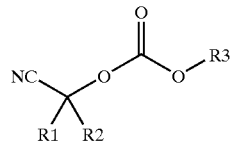

where R1 and R2 independently of one another can be an unsubstituted, monosubstituted or polysubstituted $C_1$–$C_{20}$-alkyl, $C_5$–$C_{20}$-aryl, $C_5$–$C_{20}$-heteroaryl, $C_5$–$C_{20}$-alkaryl, $C_5$–$C_{20}$-alkylheteroaryl or $C_5$–$C_{20}$-aralkyl radical or an unsubstituted, monosubstituted or polysubstituted $C_5$–$C_{20}$-heterocycle, or $C_5$–$C_{20}$-alkylheterocycle or together can be an unsubstituted or substituted $C_4$–$C_{20}$-alkylene radical, which can contain one or more heteroatoms in the chain, or one of the radicals is hydrogen, and R3 can be an unsubstituted or substituted $C_1$–$C_{20}$-alkyl, $C_5$–$C_{20}$-aryl or $C_5$–$C_{20}$-heteroaryl radical, which process comprises reacting an aldehyde or ketone of the formula

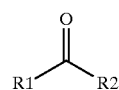

where R1 and R2 are defined as above, in the presence of an (R)- or (S)-hydroxynitrile lyase in an organic, aqueous or 2-phase system of substantially water-immiscible diluent and water or in emulsion at a temperature of –5 to +40° C. with a carbonic ester nitrile of the formula

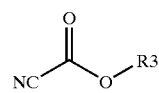

where R3 is defined as above,
to give the corresponding O-protected, enantiomer-enriched cyanohydrins of the formula (I).

2. The process as claimed in claim 1, wherein the starting materials used are compounds of the formula (II) where R1 and R2 independently of one another can be a $C_1$–$C_{20}$-alkyl, $C_5$–$C_{20}$-aryl, $C_5$–$C_{20}$-heteroaryl, $C_5$–$C_{20}$-alkaryl, $C_5$–$C_{20}$-alkyl-heteroaryl or $C_5$–$C_{20}$-aralkyl radical, or an unsubstituted, monosubstituted or polysubstituted $C_5$–$C_{20}$-heterocycle or $C_5$–$C_{20}$-alkylheterocycle or together can be an unsubstituted or substituted $C_4$–$C_{20}$-alkylene radical, which can contain one or more heteroatoms in the chain, where the radicals can be monosubstituted or polysubstituted by unsubstituted or substituted aryl or heteroaryl groups, halogen, hydroxyl, hydroxy-$C_1$–$C_5$-alkyl, $C_1$–$C_6$-alkoxy, $C_6$–$C_{20}$-aryloxy, $C_1$–$C_6$-alkylthio, amino, $C_1$–$C_6$-alkylamino, $C_6$–$C_{20}$-arylamino, ether, thioether, carboxylic ester, carboxamide, sulfoxide, sulfone, sulfonic acid, sulfonic ester, sulfinic acid, mercaptan, nitro or azido groups, or one of the radicals is hydrogen.

3. The process as claimed in claim 2, wherein the starting materials used are compounds of the formula (II) where R1 and R2 independently of one another are a saturated, unbranched or branched $C_1$–$C_8$-alkyl radical, a benzyl radical or a phenyl radical, where the radicals can be unsubstituted, monosubstituted or polysubstituted by F, Cl, OH, carboxylic esters, carboxamides, amino, $C_1$–$C_6$-alkylamino, $C_6$–$C_{20}$-arylamino, $C_1$–$C_6$-alkoxy, $C_6$–$C_{20}$-aryloxy, or nitro, or one of the radicals is hydrogen.

4. The process as claimed in claim 1, wherein the carbononitrile used is a compound of the formula (III) where R3 is a $C_1$–$C_{20}$-alkyl radical which can be substituted by one or more substituents selected from the group consisting of phenyl, $C_1$–$C_6$-alkyl, OH, halogen or sulfoxy.

5. The process as claimed in claim 1, wherein, in the case of the enantioselective reaction in an aqueous system, an aqueous solution containing the corresponding hydroxynitrile lyase or an acetate buffer, borate buffer, phthalate buffer, citrate buffer, phosphate buffer solution or a mixture of these buffer solutions is used.

6. The process as claimed in claim 5, wherein a pH of 2 to 8 is established in the aqueous solution.

7. The process as claimed in claim 1, wherein, as organic diluent, water-immiscible or only slightly water-miscible aliphatic or aromatic hydrocarbons which may be halogenated, alcohols, ethers or esters or mixtures are used.

8. The process as claimed in claim 1, wherein the reaction, however, alternatively proceeds in a two-phase system or in emulsion.

9. The process as claimed in claim 1, wherein the hydroxynitrile lyases used are native or recombinant (R)- and (S)-hydroxynitrile lyases which are present either as such or immobilized.

10. The process as claimed in claim 9, wherein the hydroxynitrile lyases used are native (S)-hydroxy-nitrile lyases from manioc and *Hevea brasiliensis*, recombinant (S)-hydroxynitrile lyase from genetically modified microorganisms from the group *Pichia pastoris, E. coli* or *Saccharomyces cerevisiae*, native (R)-hydroxynitrile lyases from *Prunus amygdalus, Prunus laurocerasus* or *Prunus serotina*, or recombinant (R)-hydroxynitrile lyases.

* * * * *